US009665693B2

(12) United States Patent
Saeger et al.

(10) Patent No.: US 9,665,693 B2
(45) Date of Patent: *May 30, 2017

(54) SYSTEM AND METHOD TO GENERATE MOLECULAR FORMULA DISTRIBUTIONS BEYOND A PREDETERMINED THRESHOLD FOR A PETROLEUM STREAM

(71) Applicant: ExxonMobil Research and Engineering Company, Annandale, NJ (US)

(72) Inventors: Roland B. Saeger, Runnemede, NJ (US); Kaiyuan He, Bridgewater, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 1008 days.

This patent is subject to a terminal disclaimer.

(21) Appl. No.: 13/834,864

(22) Filed: Mar. 15, 2013

(65) Prior Publication Data

US 2013/0325418 A1 Dec. 5, 2013

Related U.S. Application Data

(60) Provisional application No. 61/653,061, filed on May 30, 2012.

(51) Int. Cl.
*G06F 19/00* (2011.01)
*G01N 33/28* (2006.01)

(52) U.S. Cl.
CPC .......... *G06F 19/701* (2013.01); *G06F 19/704* (2013.01); *G01N 33/2823* (2013.01)

(58) Field of Classification Search
None
See application file for complete search history.

(56) References Cited

U.S. PATENT DOCUMENTS 5,446,681 A * 8/1995 Gethner ............... G01N 21/359
702/27
5,817,517 A * 10/1998 Perry ................... C10G 11/187
250/339.12

(Continued)

OTHER PUBLICATIONS

McKenna et al., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Doduszynski Model, Energy & Fuels, Vol. 24, pp. 2429-2938 (2010).

(Continued)

*Primary Examiner* — Omar Fernandez Rivas
*Assistant Examiner* — Herng-der Day
(74) *Attorney, Agent, or Firm* — Glenn T. Barrett; Andrew T. Ward

(57) ABSTRACT

Methods for generating molecular formula distributions beyond a predetermined threshold for a petroleum stream are disclosed. An initial molecular formula distribution within a predetermined threshold is obtained for a petroleum stream. A correlation between two or more molecular properties of the initial molecular formula distribution is identified, and the initial molecular formula distribution is extrapolated beyond the predetermined threshold along the correlation. The extrapolated molecular formula is renormalized based on renormalization data obtained from the sample. The renormalized molecular formula distribution can then be blended with the initial molecular formula distribution, reconciled to secondary analytical measurements, and/or used to create a model of composition and/or a molecular composition-based model of a resid upgrading process. Systems for implementing the methods are also disclosed.

37 Claims, 14 Drawing Sheets

(56) References Cited

U.S. PATENT DOCUMENTS

| | | | |
|---|---|---|---|
| 6,662,116 B2* | 12/2003 | Brown | G01N 21/35 436/29 |
| 7,598,487 B2 | 10/2009 | Qian et al. | |
| 7,619,217 B2 | 11/2009 | Shea et al. | |
| 2009/0105966 A1 | 4/2009 | Brown et al. | |
| 2013/0055795 A1 | 3/2013 | Chawla et al. | |
| 2013/0325362 A1* | 12/2013 | Saeger | G06F 19/704 702/25 |

OTHER PUBLICATIONS

McKenna et al., "Heavy Petroleum Composition. 2. Progression of the Boduszynski Model to the Limit of Distillation by Ultrahigh-Resolution FT-ICR Mass Spectrometry", Energy & Fuels, vol. 24, pp. 2939-2946 (2010).

Quann et al., "Structure-Oriented Lumping: Describing the Chemistry of Complex Hydrocarbon Mixtures", Industrial & Engineering Chemistry Research, vol. 31, pp. 2483-2497 (1990).

U.S. Appl. No. 61/653,069, filed May 30, 2012.

The International Search Report and Written Opinion of PCT/US2013/041494 dated Feb. 10, 2014.

Qian et al., "Determination of Structural Building Blocks in Heavy Petroleum Systems by Collision-Induced Dissociation Fourier Transform Ion Cyclotron Resonance Mass Spectrometry," Analytical Chemistry, 2012, vol. 84, No. 10, pp. 4544-4551.

Jaffe et al., "Extension of Structure-Oriented Lumping to Vacuum Residua," Ind. Eng. Chem. Res., 2005, vol. 44, pp. 9840-9852.

Schaub et al., "Speciation of Aromatic Compounds in Petroleum Refinery Streams by Continuous Flow Field Desorption Ionization Ft-Icr Mass Spectrometry," Energy & Fuels, 2005, vol. 19, pp. 1566-1573.

\* cited by examiner

CONTINUED-1

CONTINUED-2

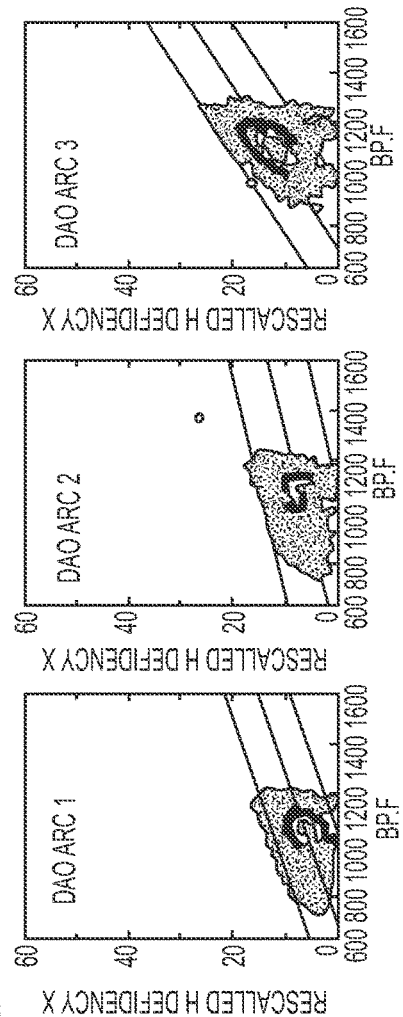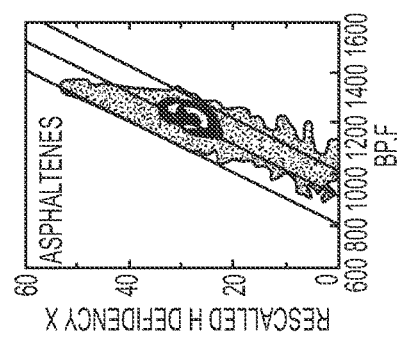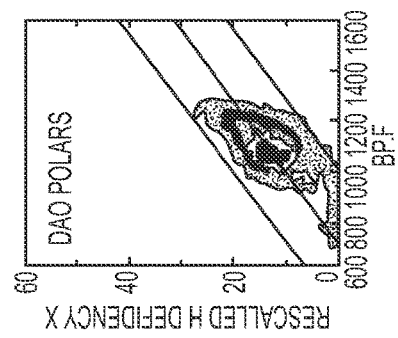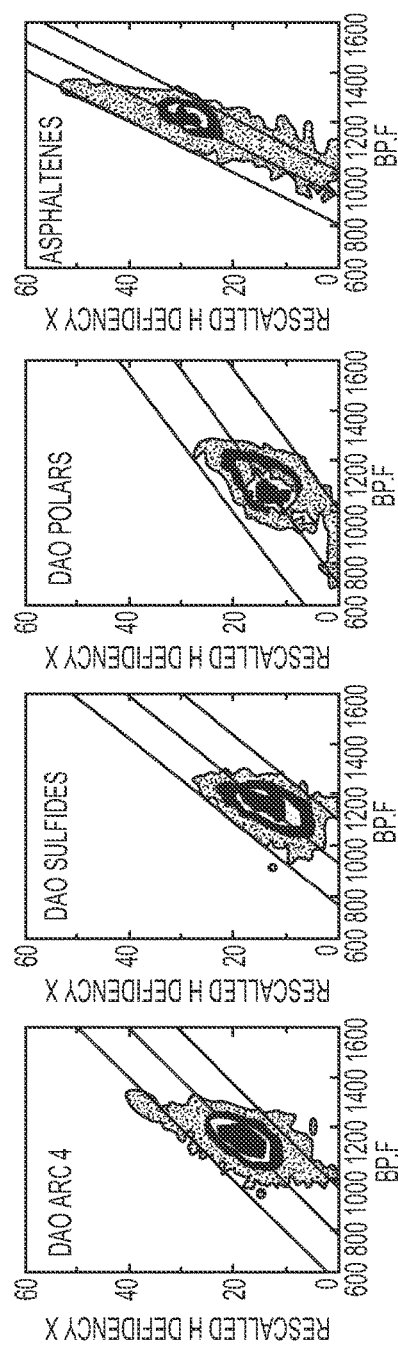
FIG. 6A  FIG. 6B  FIG. 6C  FIG. 6D  FIG. 6E  FIG. 6F  FIG. 6G
SOLID LINE: MEAN BOILING POINT BP EXTRAPOLATION
$BP = \overline{BP}(X) \pm 3\sigma_{BP}$
DASHED LINES:

SYSTEM AND METHOD TO GENERATE MOLECULAR FORMULA DISTRIBUTIONS BEYOND A PREDETERMINED THRESHOLD FOR A PETROLEUM STREAM

BACKGROUND OF THE INVENTION

Field of the Invention

The present application generally relates to systems and methods for generating molecular formula distributions and models of composition to accommodate limitations of current measurement methods. For example, the systems and methods disclosed herein can be used to extrapolate a molecular formula distribution beyond a boiling point threshold or similar limitation.

Description of Related Art

Petroleum streams are complex mixtures of hydrocarbons containing enormous numbers of distinct molecular species. These streams include a variety of hydrocarbon streams from processes directed to the petroleum molecular composition. For example, virgin petroleum crude oils can contain molecules of a wide boiling point range from highly volatile C4 hydrocarbons to nonvolatile asphaltenes. The streams are extremely complex, and have numerous distinct molecular species. As such, any molecular approximation of the composition is essentially a model, that is, a model of composition (MoC). Analysis of petroleum composition of various boiling points is necessary for inputs to many subsequent processes.

Fourier Transform Ion Cyclotron Resonance (FTICR) mass spectrometry, together with a suitable ionization method, can be used in constructing an initial estimate of the composition of a petroleum stream. Ionization methods used in conjunction with FTICR include Atmospheric Pressure Photoionization (APPI) and negative and positive ion electrospray (N-, PESI).

Despite FTICR's ultra-high mass resolution, this technique alone cannot provide sufficient information to construct an accurate model of composition beyond certain thresholds. For example, none of the identified ionization methods can efficiently ionize molecules in complex hydrocarbon mixtures that boil above 1250° F. Thus, known techniques cannot provide sufficient information to construct a Heavy Hydrocarbon Model of Composition (HH-MoC) that is consistent with all features of the petroleum stream. HHMoC, as used herein, refers to a model of composition for a vacuum residuum (also known as resid) stream, i.e., petroleum streams that boil above 1000° F. In at least some resid streams, at least 50 weight percent of the molecules are known to boil above 1250° F. Thus, current ultrahigh resolution APPI-FTICR-MS (or N—, PESI-FTICR-MS) data does not lead to accurate estimates of molecular property distributions on the entire resid, or the entire resid fraction. Examples of FTICR-MS data based on the current technique are disclosed in available literature. See, e.g., McKenna, A. M., et al., "Heavy Petroleum Composition. 1. Exhaustive Compositional Analysis of Athabasca Bitumen HVGO Distillates by Fourier Transform Ion Cyclotron Mass Spectrometry: A Definitive Test of the Doduszynski Model," Energy & Fuels, v. 24, pp. 2429-2938, 2010.

Furthermore, APPI-FTICR-MS has poor ionization efficiency for molecules that boil above 1250° F. Relative to high-temperature Simdis measurements, FTICR severely under-predicts the amount of material boiling above 1250 F.

Hence, it is not uncommon for FTICR to be unable to detect approximately 40 weight percent of the highest boiling material of a resid.

Therefore, there is a need for a system and method to extrapolate a significant portion of the FTICR mass spectrum to higher boiling points such that it is suitable for HHMoC applications.

SUMMARY OF THE INVENTION

The purpose and advantages of the present application will be set forth in and apparent from the description that follows, as well as will be learned by practice of the disclosed subject matter. Additional advantages of the disclosed subject matter will be realized and attained by the method and apparatus particularly pointed out in the written description and claims hereof, as well as from the appended drawings.

To achieve these and other advantages and in accordance with the purpose of the application, as embodied and broadly described, the disclosed subject matter includes a method to generate molecular formula distributions beyond a predetermined threshold for a petroleum stream. The method can include the steps of obtaining an initial molecular formula distribution within a predetermined threshold for a sample of a petroleum stream, identifying a correlation between two or more molecular properties of the initial molecular formula distribution, extrapolating, using at least one processor, the initial molecular formula distribution beyond the predetermined threshold to construct an extrapolated molecular distribution, and renormalizing the extrapolated molecular formula distribution based on renormalization data obtained from the sample to generate a renormalized molecular formula distribution.

For example, the two or more molecular properties can include hydrogen deficiency, boiling point, molecular weight, molecular fraction, and molecular type. Likewise, the renormalization data obtained for the sample can be, for example, FDMS, BP distribution, GC-Simdis, or molecular type distribution.

In accordance with one embodiment of the disclosed subject matter, an analytical technique is used to obtain the initial molecular formula distribution. The analytical technique can be, for example, high-detail hydrocarbon analysis, micro-hydrocarbon analysis, or ultrahigh resolution Fourier Transform Ion Cyclotron Resonance mass spectrometry. The analytical technique can also be a multivariate analytical technique.

In accordance with another embodiment of the disclosed subject matter, a modeling technique can be used to obtain the initial molecular formula distribution. The modeling technique can be, for example, a composition-based process modeling technique, a composition synthesis modeling technique, or a theory-based modeling technique.

As disclosed herein, the initial molecular formula distribution can be expressed as a fraction molecular formula distribution for each of a plurality of fractions. Each of the plurality of fractions can be, for example, a liquid chromatographic fraction. The plurality of fractions can include one or more of DAO saturates, DAO ARC1, DAO ARC2, DAO ARC3, DAO ARC4, DAO sulfides, DAO polars, asphaltenes, DAO aromatics, and DAO.

In accordance with another aspect of the disclosed subject matter, the initial molecular formula can be seeded with, for example, at least one metal containing molecule. The metal containing molecule can include, for example, a nickel-containing porphyrin or a vanadium-containing porphyrin.

In accordance with another embodiment of the disclosed subject matter, the correlation between the two or more molecular properties can include calculating a coefficient of an equation defining a first molecular property as a function of a second molecular property. The coefficient can be calculated, for example, using a least squares analysis. The equation can be, for example, a linear equation, a non-linear equation, or an equation selected to conserve a desired property of the petroleum stream. The desired property can be, for example, hydrogen content, percent aromatic carbon, heteroatom content, or a solubility parameter. In some embodiments, a standard deviation of at least one of the two or more molecular properties can be calculated.

As disclosed herein, extrapolating the initial molecular formula distribution can include calculating a normal distribution of a first molecular property and mapping the normal distribution of the first molecular property from a first space to a second space. Alternatively, extrapolating the initial molecular formula distribution can include extending the initial molecular formula distribution along a line defined by the correlation. The extrapolated molecular formula distribution can be bounded by an upper bound and a lower bound calculated based on the line and a standard deviation of at least one of the two or more molecular properties.

In another embodiment of the disclosed subject matter, renormalizing the extrapolated molecular formula distribution can include scaling the extrapolated molecular formula distribution and matching a total abundance by molecular type of the extrapolated molecular formula distribution with a total abundance of a measurement of the sample. The measurement can be, for example, a FTICR-MS measurement.

In accordance with another aspect of the disclosed subject matter, the method can include blending the renormalized molecular formula distribution with the initial molecular formula distribution. Blending can include, for example, determining a first discrete distribution for the initial molecular formula distribution and a second discrete distribution for the renormalized molecular formula distribution, normalizing the first discrete distribution by matching a peak abundance of the normalized first discrete distribution with a peak abundance of the second discrete distribution, identifying an interpolation function based on the normalized first discrete distribution and the second discrete distribution, and generating a blended molecular formula distribution based on the interpolation function.

Furthermore, and in accordance with an additional aspect of the disclosed subject matter, the method can include reconciling the renormalized molecular formula distribution with a secondary analytical measurement. The secondary analytical measurement can be, for example, super critical fluid chromatography, sulfur simulated distillation, simulated distillation, N and S elemental analysis, H-NMR and GC-Flame Ionization Detection. The method can further include creating a model of composition based on the reconciled molecular formula distribution.

In accordance with an additional aspect of the disclosed subject matter, the method can include creating a molecular composition-based process model of a resid upgrading process based on the renormalized molecular formula distribution. The resid upgrading process can include, for example, thermal cracking (coking), propane-deasphalting, and hydroprocessing.

Also disclosed herein is a system to generate a molecular formula distribution for a petroleum stream beyond a predetermined threshold. The system can include a receiver for an initial molecular formula distribution within a predetermined threshold obtained from a sample of a petroleum stream, a correlation unit to identify a correlation between two or more molecular properties of the initial molecular formula distribution, an extrapolation unit to extrapolate the initial molecular formula distribution beyond the predetermined threshold along the correlation to construction an extrapolated molecular distribution, and a renormalization unit to renormalize the extrapolated molecular formula distribution based on renormalization data obtained from the sample to generate a renormalized molecular formula distribution. Additional aspects and features of the system are described in conjunction with the method.

BRIEF DESCRIPTION OF THE DRAWINGS

FIGS. 6a-6g are graphs showing an initial molecular formula plotted against a correlation and an upper and lower bound in accordance with one embodiment of the disclosed subject matter.

FIGS. 10a and 10b are schematic representations of a method for blending the initial molecular formula with the renormalized molecular formula, wherein FIG. 10a is a graph showing the discrete boiling point distributions for the initial molecular formula distribution and the renormalized molecular formula distribution, and FIG. 10b is a graph showing the discrete boiling point distribution for the renormalized molecular formula distribution and the normalized discrete boiling point distribution for the initial molecular formula distribution.

DETAILED DESCRIPTION OF THE PREFERRED EMBODIMENT

Figure 1:
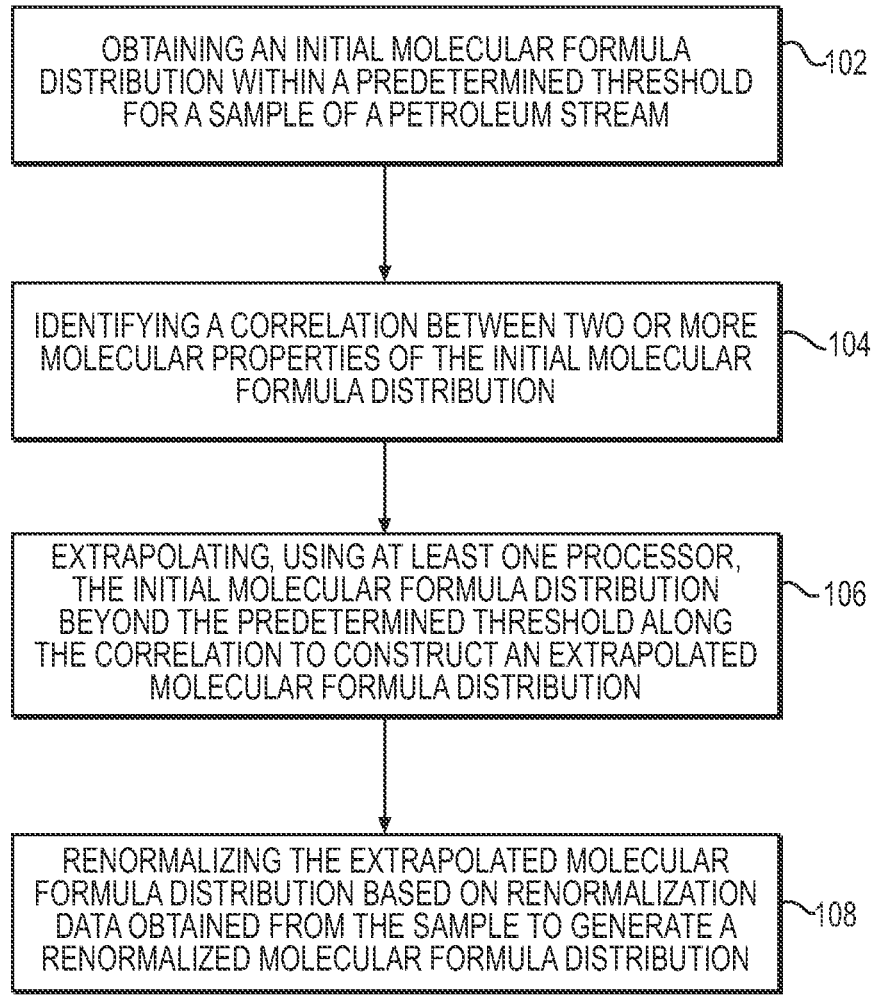
FIG. 1 is a flow chart of a representative embodiment of a method of extrapolating a molecular formula distribution beyond a predetermined threshold in accordance with the disclosed subject matter.

Reference will now be made in detail to the present preferred embodiments of the disclosed subject matter, examples of which are illustrated in the accompanying drawings. The systems and method herein generally are intended for evaluating the composition of a petroleum stream, although other similar or suitable uses are contemplated.

In accordance with the disclosed subject matter, a method to extrapolate molecular formula distributions beyond a predetermined threshold is provided. The method generally includes obtaining an initial molecular formula distribution within a predetermined threshold for a sample of a petroleum stream; identifying a correlation between two or more molecular properties of the initial molecular formula distribution; extrapolating, using at least one processor, the initial molecular formula distribution beyond the predetermined threshold to construct an extrapolated molecular distribution; and renormalizing the extrapolated molecular formula distribution based on renormalization data obtained from the sample to generate a renormalized molecular formula distribution.

Likewise, and in accordance with another aspect of the disclosed subject matter, a system to generate molecular formula distributions beyond a predetermined threshold for a petroleum stream is provided. The system includes a receiver for an initial molecular formula distribution within a predetermined threshold obtained from a sample of a petroleum stream, a correlation unit to identify a correlation between two or more molecular properties of the initial molecular formula distribution, an extrapolation unit to extrapolate the initial molecular formula distribution beyond the predetermined threshold along the correlation to construction an extrapolated molecular distribution, and a renormalization unit to renormalize the extrapolated molecular formula distribution based on renormalization data obtained from the sample to generate a renormalized molecular formula distribution.

For purposes of explanation and illustration, and not limitation, an exemplary embodiment of the method in accordance with the application is shown in FIGS. 1 through 11. Furthermore, and for the purpose of understanding, reference and description of the system will be made in conjunction with the description of the method disclosed herein.

The systems and methods disclosed herein are generally described with reference to extrapolating a molecular formula distribution beyond a predetermined boiling point threshold. However, one having skill in the art will appreciate that other molecular properties can be used as the predetermined threshold with suitable adjustments. The predetermined threshold can be, for example, a molecular weight threshold or a hydrogen deficiency threshold.

The systems and methods disclosed herein are also generally described with reference to extrapolating a fraction molecular formula distribution for a plurality of fractions. The fraction can be of any suitable size, number, and characteristic. Furthermore, the disclosed subject matter also encompasses the extrapolation of a molecular formula distribution for the sample of the petroleum stream as a whole.

As such, the molecular properties used in constructing the correlation can include the boiling point of the entire petroleum stream and the boiling point of one or more fractions (e.g., each liquid chromatographic fraction).

In accordance with one embodiment of the method and system disclosed herein, the initial molecular formula distribution can be determined using an analytical technique. For example, and not limitation, and with reference to FIG. 1, an initial molecular formula distribution within a predetermined threshold for a sample of a petroleum stream is obtained (See 102). For purpose of illustration, the molecular formula is given by $C_cH_{2c+z}S_sN_nO_oNi_{ni}V_v$, where a molecule's carbon number is c; its hydrogen deficiency class is Z; and s, n, o, ni, and v are the stoichiometric coefficients of sulfur, nitrogen, oxygen, nickel, and vanadium, respectively. Molecular formula distribution can be expressed mathematically in suitable units, such as weight percent abundance of molecular lumps. The weight percent abundance of the molecular lump can be expressed as w(f,MW,Z,T), where f is the fraction index; MW is the nominal molecular weight; Z is the hydrogen deficiency class; and T is the molecular type.

The fraction index f can correspond to any subgrouping of the sample. In one embodiment, for illustration and not limitation, the fraction index f corresponds to liquid chromatographic fractions as shown in Table 1.

TABLE 1

| Fraction | Fraction Index, f |
|---|---|
| DAO Saturates | 1 |
| DAO ARC 1 | 2 |
| DAO ARC 2 | 3 |
| DAO ARC 3 | 4 |
| DAO ARC 4 | 5 |
| DAO Sulfides | 6 |
| DAO Polars | 7 |
| Asphaltenes | 8 |
| DAO Aromatics | 9 |
| DAO | 10 |
| Resid | 11 |

Molecular type, T, depends on the stoichiometric coefficients of heteroatoms s, n, o, and of metals ni, v. Examples of molecular types T are shown in Table 2.

TABLE 2

| | Stoichiometric Coefficient | | | | |
|---|---|---|---|---|---|
| Type | s | n | o | ni | v |
| HC | 0 | 0 | 0 | 0 | 0 |
| 1S | 1 | 0 | 0 | 0 | 0 |
| 1O | 0 | 0 | 1 | 0 | 0 |
| 1S2N | 1 | 2 | 0 | 0 | 0 |
| 3S1N1O | 3 | 1 | 1 | 0 | 0 |
| 4N1Ni | 0 | 4 | 0 | 1 | 0 |
| 1S4N1O1V | 1 | 4 | 1 | 0 | 1 |

Nominal molecular weight, MW, can take on any positive integer. In some embodiments, nominal molecular weights can be truncated above a reference molecular weight. Hydrogen deficiency class Z takes integers 2, 1, 0, . . . $-\infty$. For molecules having an even number of nitrogen atoms, i.e., the stoichiometric index n=0, 2, 4, . . . , the hydrogen deficiency class Z and the nominal molecular weight MW are even integers. For molecules with an odd number of nitrogen atoms, i.e., n=1, 3, 5, . . . , hydrogen deficiency class Z and molecular weight MW are odd integers.

Furthermore, a single fraction can be a composite of other fractions. For example, for purpose of illustration in Table 1, the molecular formula distribution of the DAO Aromatics fraction is the sum of the molecular formula distributions in the DAO ARC fractions:

$$w(9,MW,Z,T) = \Sigma_{f=2,3,4,5} w(f,MW,Z,T) \qquad (1)$$

The molecular formula distribution of the DAO fraction is the sum of the molecular formula distributions in each of the silica-gel separation fractions:

$$w(10,MW,Z,T) = \Sigma_{f=1,6,7,9} w(f,MW,Z,T) \qquad (2)$$

The resid, labeled with a fraction index of 11 in Table 1, is the sample of the petroleum stream as a whole. Thus, the molecular formula distribution of the resid is the sum of the molecular formula distributions in the DAO and asphaltene fractions:

$$w(11,MW,Z,T) = \Sigma_{f=8,10} w(f,MW,Z,T) \qquad (3)$$

The initial molecular formula can be obtained using an analytical technique. The analytical technique can be a multivariate analytical technique or any other analytical technique known in the art for its intended purpose. These techniques can include, for example, high-detail hydrocarbon analysis (HDHA), micro-hydrocarbon analysis (MHA), or ultrahigh resolution Fourier-transform Ion Cyclotron Resonance Mass Spectrometry (FTICR-MS). HDHA can be used to analyze complex hydrocarbon mixtures that boil below 1000° F. MHA is a similar analytical technique, but enables the analysis of selected hydrocarbon mixtures using smaller sample volumes than HDHA. MHA is more fully described in U.S. Pat. No. 7,598,487, which is incorporated herein by reference in its entirety.

Ultrahigh resolution FTICR-MS can be used in conjunction with a number of ionization methods. These ionization methods can include, for example, Atmospheric Pressure Photoionization (APPI), Negative and Positive-Ion Electrospray Ionization (NESI or PESI), Matrix-Assisted Laser Dissociation Ionization (MALDI), Desorption Electrospray Ionization (DESI), and Laser Induced Acoustic Desorption (LIAD). LIAD is described in greater detail in U.S. Pat. No. 7,619,217.

Alternatively, and in accordance with another embodiment, the initial molecular formula distribution can be obtained using a modeling technique. The modeling technique can be, for example, composition-based process modeling, which creates the molecular formula distribution as the molecular formula distribution of a product or intermediate stream whose composition is computed within a process model. The modeling technique can also be composition synthesis modeling, wherein the molecular formula distribution is derived from analytical techniques, but has been adjusted to match its own bulk properties, or that of another hydrocarbon stream. The modeling technique can also be theory-based modeling, wherein the distribution of molecules, and hence molecular formulae, is predicted by a theory that can be reduced to a computer-based algorithm. An example of a theory-based modeling technique is the Anderson-Schulz-Flory distribution arising in Fischer-Tropsch synthesis. A more complex example is petroleum, whose molecular distributions can be approximated by combining geochemical-based rules of formation, e.g., isoprene alkylation, biodegradation, thermo-chemical sulfate reduction.

The term "obtain," as used herein with reference to the initial molecular formula distribution, broadly encompasses measuring the molecular formula distribution using one of the analytical techniques, generating the molecular formula distribution using a modeling technique, receiving the molecular formula distribution from another resource, and/or generating a molecular formula distribution based in whole or in part on the information received from another resource.

Figure 2:
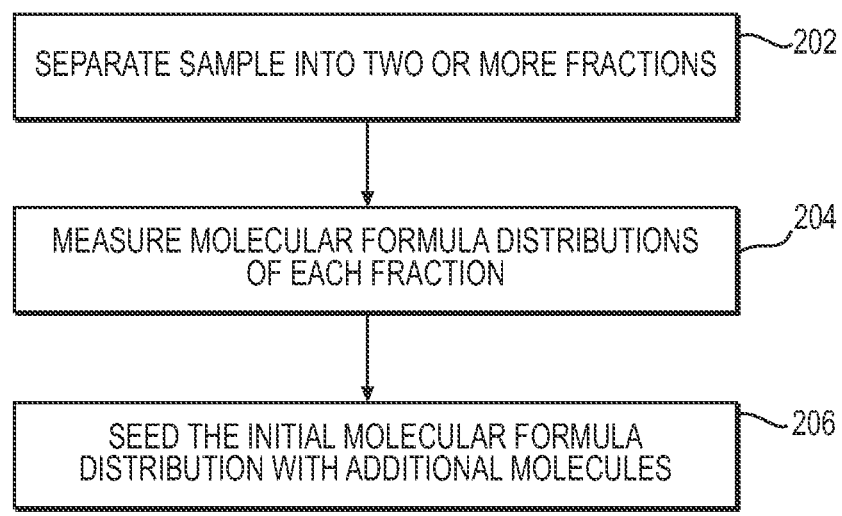
FIG. 2 is a flow chart of a representative embodiment of a method of obtaining an initial molecular formula distribution in accordance with the disclosed subject matter.
Figure 3:
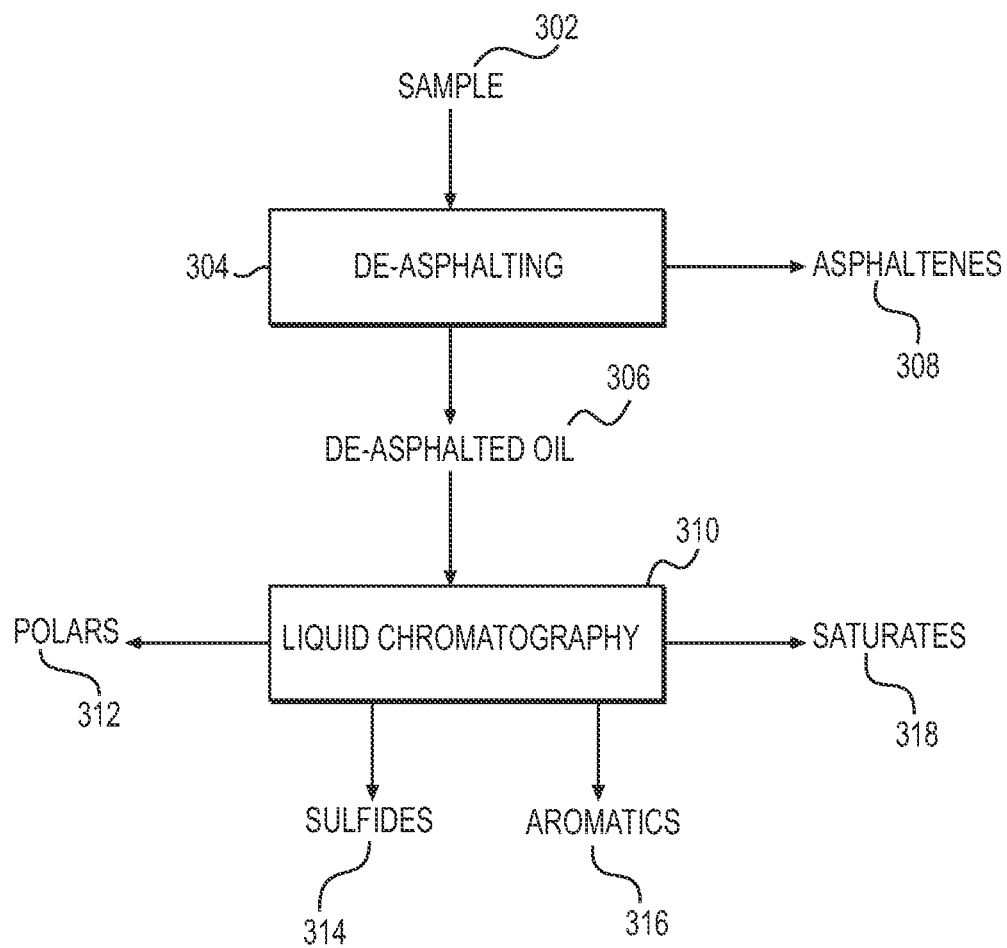
FIG. 3 is a flow chart of a representative embodiment of a method of separating a sample of the petroleum stream into two or more fractions in accordance with the disclosed subject matter.

FIG. 2 illustrates an exemplary embodiment of a method for obtaining an initial molecular formula distribution in accordance with the disclosed subject matter. As shown in FIG. 2, the initial molecular formula can be expressed as a fraction molecular formula distribution for each of a plurality of fractions. For example, and not limitation, a sample of the petroleum stream is separated into two or more fractions. (See 202). The fractions can be, for example, liquid chromatography fractions. An exemplary embodiment of the separation process is shown in FIG. 3.

A sample of the petroleum stream 302 is introduced to a de-asphalting process 304. The de-asphalting process 304 separates the sample 302 into de-asphalted oil (DAO) 306 and asphaltenes 308. The de-asphalted oil is then introduced to a liquid chromatography process 310. This process separates the de-asphalted oil into DAO polars 312, DAO sulfides 314, DAO aromatics 316, and DAO saturates 318. Each of the DAO subfractions 312, 314, 316, and 318 can be further separated as desired. For example, the DAO aromatics can be further separated into aromatic ring classes (ARC) 1-4. This exemplary separation protocol is described in greater detail in U.S. patent application Ser. No. 13/223,739, entitled "Fractionation of De-Asphalted Oil of Vacuum Resid Using Preparative High Performance Liquid Chromatographic Separations", which is incorporated by reference herein in its entirety for all purposes.

With further reference to FIG. 2, the molecular formula distribution of each fraction is then measured (See 204). The molecular formula distribution can be measured, for example, using FTICR-MS analysis. Each fraction of the material can be analyzed by the FTICR and a molecular formula distrubution for each fraction can be output. In one embodiment, the molecular formula distribution derived from the FTICR-MS analysis is reported as a triplet of three attributes: the molecule's nominal mass, MW (e.g., in g/mol), its hydrogen deficiency class, Z, and its molecular type, T.

If desired or necessary, the initial molecular formula can be "seeded" with additional molecules. (See 206). That is, certain measurement techniques may not correctly identify each type of molecule present in a sample. For example, metals analysis (ASTM D 5708) of DAO and asphaltene fractions detect ppm quantities of both nickel and vanadium in some measured samples. However, APPI-FTICR-MS is not capable of detecting organometallic (porphyrin) compounds in all such measured samples. To reconcile these molecular formula distributions to metals analysis, the initial molecular formula distribution can be seeded with at least one metal-containing molecule. For example, porphyrin compounds can be seeded into FTICR-MS data. In asphaltene fractions, where porphyrin seeding is desired, vanadium-containing porphyrins can taken from APPI-FTICR-MS analysis of the asphaltene fraction of a reference sample. The reference sample can be, for example, a well-known and widely-traded petroleum stream. In DAOs where porphyrin seeding is desired, vanadium-containing porphyrins can be taken from APPI-FTICR analysis of one of the fractions (e.g., the DAO ARC4 fraction) of the same or a different reference sample. After seeding, the weight percent abundance of these vanadyl porphyrins in each fraction can be renormalized to a reference abundance. The reference abundance can be, for example, a total abundance of about 10 ppm. Nickel-containing porphyrins may not be detectable in a reference sample, and thus can be synthesized from vanadyl porphyrins in each of the DAO ARC4 and asphaltene fractions. For example, if seeding of nickel-containing porphyrins is desired for molecular types 4N1Ni and 1S4N1Ni, the nickel-containing porphyrins can be synthesized using Equations 4 and 5.

$$w_{os}(f,4N1Ni,MW-8,Z) = w_0(f,4N1O1V,MW,Z) \quad (4)$$

$$w_{os}(f,1S4N1Ni,MW-8,Z) = w_0(f,1S4N1O1V,MW,Z) \quad (5)$$

for f=5, 8, where $w_0$ is the initial molecular formula distribution and $w_{os}$ is the seeded molecular formula distribution. As used herein, the term initial molecular formula distribution includes the seeded molecular formula distribution, except where such difference is made explicit, as these terms are used solely for reference.

Synthesis of nickel-containing porphyrins from vanadyl porphyrins is equivalent to replacing the V and O atoms with Ni, thus decreasing the molecular weight of the porphyrin by 51+16−59=8 g/mol. The replacement does not change the number of hydrogen atoms in the porphyrin, and therefore the hydrogen deficiency class, Z, is unaffected.

Figure 4:
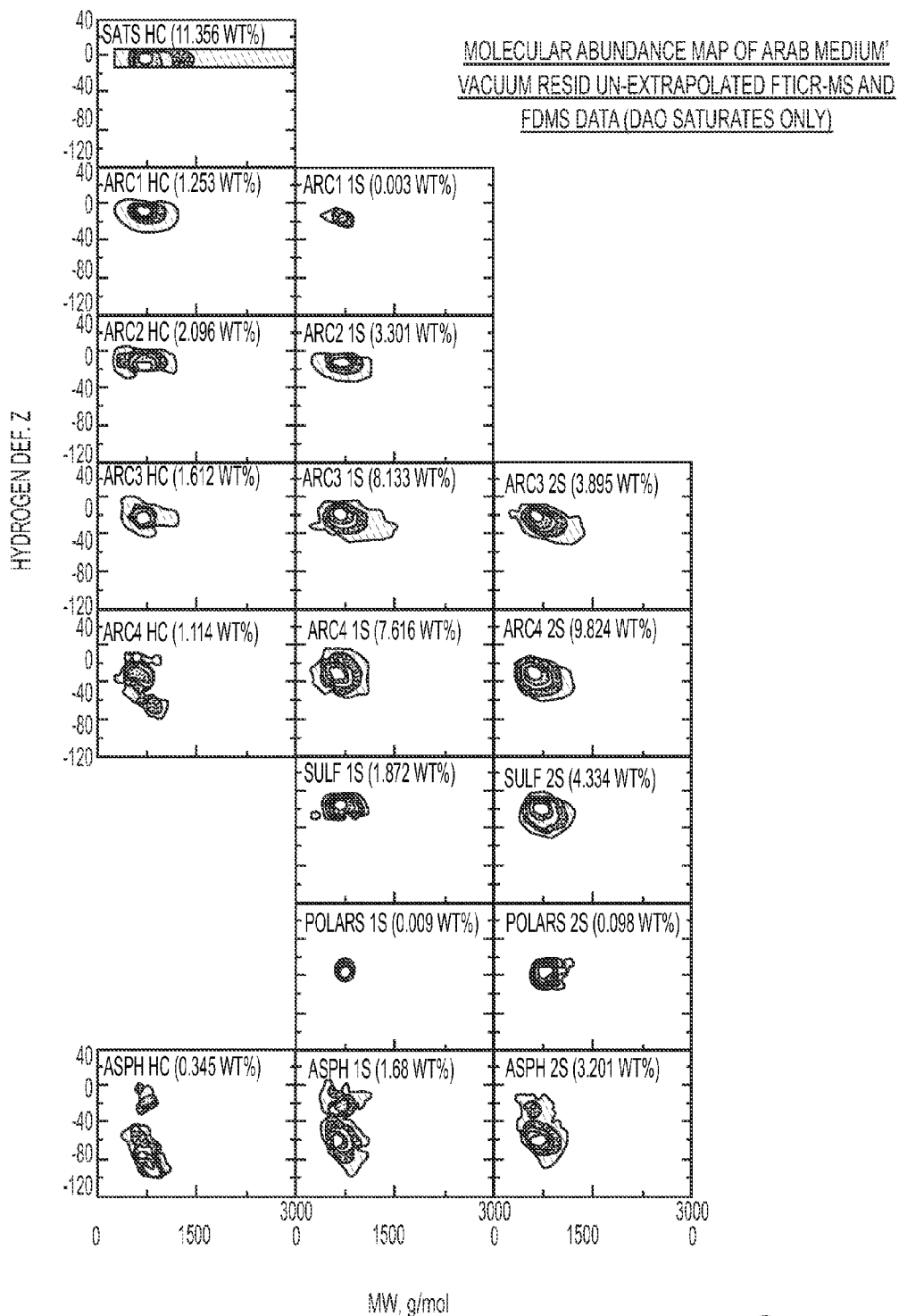
FIG. 4 is an array of plots showing a representative embodiment of an initial molecular formula distribution in accordance with the disclosed subject matter.
Figure 4:
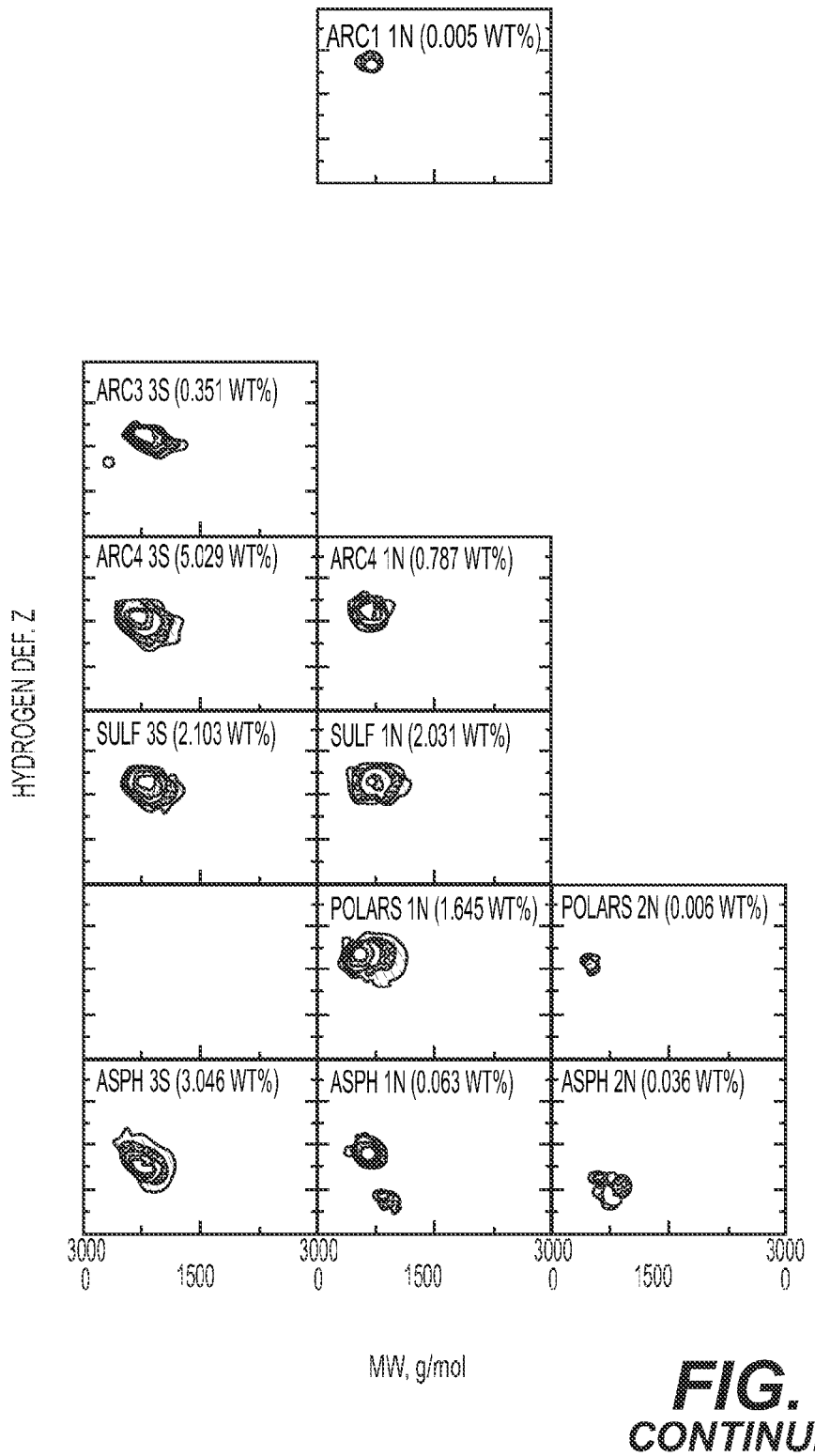
Figure 4:
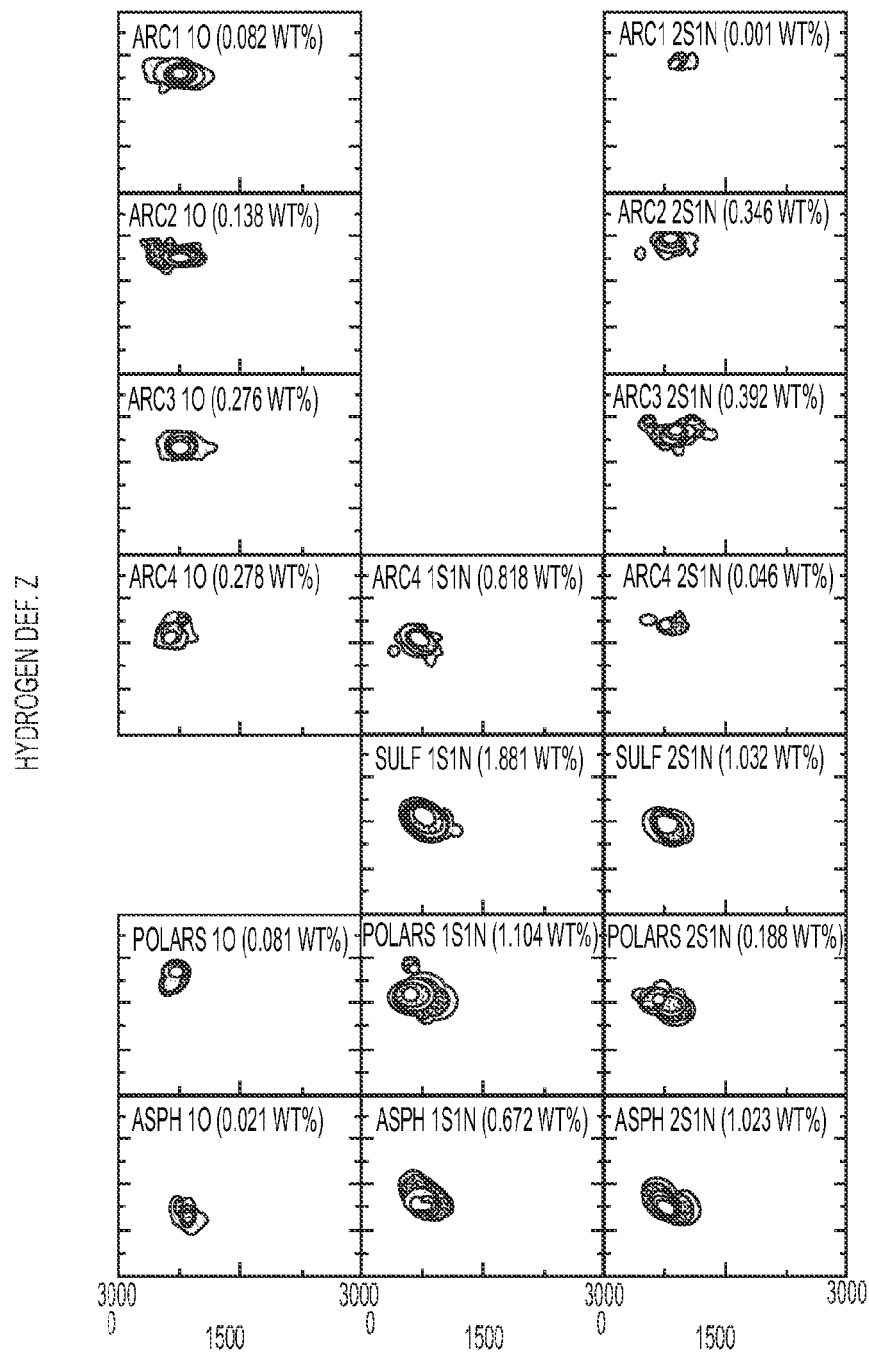

The molecular formula distributions of the sample, or of each fraction in the sample, can be visualized as an array of plots, as shown in FIG. 4. The plots show the total abundance (in weight percent on a total sample basis) within each fraction and molecular type combination.

Figure 5:
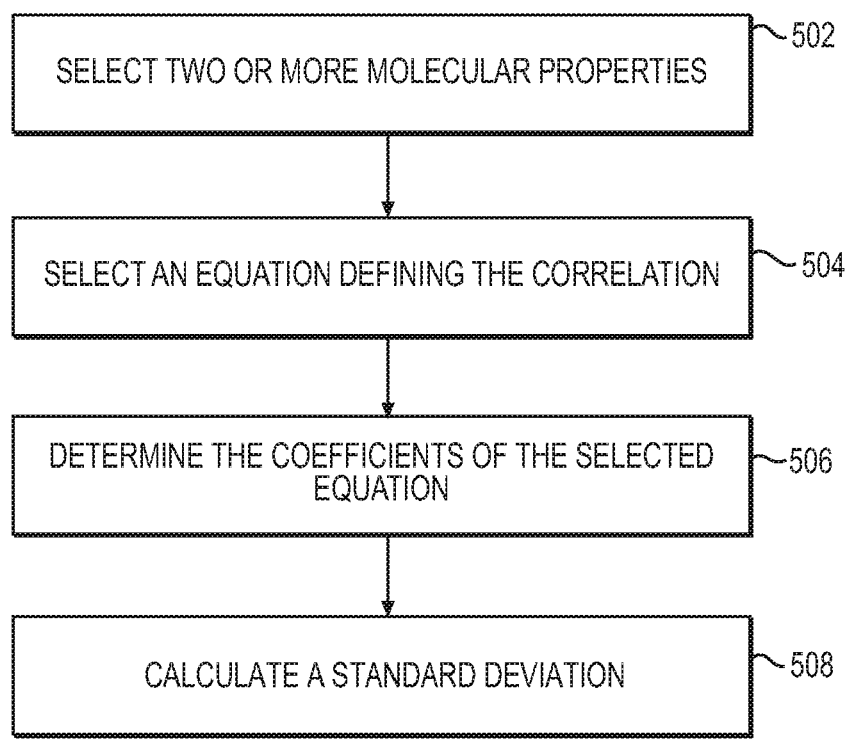
FIG. 5 is a flow chart of a representative embodiment of a method of identifying a correlation between two or more molecular properties in accordance with the disclosed subject matter.

With further reference to FIG. 1, a correlation between two or more molecular properties of the initial molecular formula distribution can be identified. (See 104). A variety of techniques to identify the correlation can be used. For example, in one embodiment, identifying the correlation seeks to maintain the relative abundances in each fraction and molecular type combination as previously determined, such as shown in FIG. 4. An example of one such method is shown in FIG. 5. First, the two or more molecular properties to be correlated are selected. (See 502). For example, and not limitation, the correlated molecular properties can include hydrogen deficiency class and the weight-averaged boiling point of the entire sample; hydrogen deficiency class, the weight-averaged boiling point of the entire sample, and molecular type; hydrogen deficiency class and the weight-averaged molecular weight of the entire sample; hydrogen deficiency class and the weight-averaged boiling point of each liquid chromatographic fraction; and hydrogen deficiency class and the weight-averaged molecular weight of each liquid chromatographic fraction.

With further reference to FIG. 5, an equation defining the correlation is selected. (See 504). The equation can define a first molecular property as a function of a second molecular property. For example, if the selected molecular properties are hydrogen deficiency class and weight-averaged boiling point of the entire sample, the equation can define the hydrogen deficiency class as a function of the weight-averaged boiling point of the entire sample and a number of constants. The equation can be chosen to conserve a desired property. Hence, the equation can be a linear equation or a non-linear equation.

The equation can be chosen by identifying a convenient molecular property. For example and illustration, and not limitation, a convenient molecular property X is defined in one embodiment as:

$$X = (\text{mod}(Z,2) - Z)/2 \quad (6)$$

where Z is the hydrogen deficiency class of each molecule that can be computed from its molecular formula.

For molecules in each of the liquid chromatographic fractions identified in Table 1, the convenient molecular property X correlates well with boiling point, where each molecular boiling point has been computed from its molecular formula using a model. The model can be, for example, a model based on a correlation between molecular formula and boiling point. Therefore, the correlation between X and boiling point can be defined as:

$$X \cong a + b\text{BP}_{mean} \quad (7)$$

where $\text{BP}_{mean}$ is the weight-averaged boiling point, and a and b are the coefficients. The weight-averaged boiling point can be defined, for example, as:

$$BP_{mean}(f, X) = \\ 0.01 \sum_{T} \sum_{MZ} w_0(f, MW, Z(X, T), T) BP(MW, Z(X, T), T) \quad (8)$$

In another embodiment, a non-linear equation can be used to correlate the two or more molecular properties. In one embodiment, the correlation can be defined as:

$$X \cong a + b\text{BP}_{mean} + c(\text{BP}_{mean})^2 \quad (9)$$

where X is defined as in Equation 6; $\text{BP}_{mean}$ is the weight-averaged boiling point; and a, b, and c are the coefficients. The equations disclosed herein are provided for example, and not by way of limitation. In view of the examples provided above, it is recognized that a wide variety of equations can be chosen for use in correlating the two or more molecular properties. The equation chosen will often be dependent upon the two or more molecular properties chosen, such that steps 502 and 504 of FIG. 5 can be combined into a single step.

With further reference to FIG. 5, the coefficients of the selected equation are calculated. (See 506). The coefficients can be calculated, for example, by mathematical analysis based on measurement data. For example, coefficients a and b of Equation 7 can be determined by a least-squares analysis based on the measured FTICR-MS data for the sample. In general, the mathematical analysis can be any suitable technique for its intended purpose as known in the art.

In some instances, the slope b of Equation 7 can be calculated as a negative number. In this case, the extrapolation of the initial molecular formula distribution is not necessary (i.e., $w_0(f, MW, Z, T) = w*(f,MW,Z,T)$), where $w*(f,MW,Z,T)$ is the molecular formula distribution used in, for example, generating a model of composition.

In another embodiment, the coefficients are determined in such a way as to match the molecular formula to a desired property of the sample or a fraction thereof. For example, with reference to Equation 9, coefficients a and b can be determined using a mathematical analysis, e.g., a least-squares analysis, while coefficient c can be determined iteratively to match the molecular formula distribution to a desired property. The desired property can be, for example, hydrogen content of the sample or a fraction thereof, percent aromatic carbon of the sample or a fraction thereof, heteroatom content of the sample or a fraction thereof, and a solubility parameter of the sample or a fraction thereof. The heteroatom content can be, for example, percent sulfur, percent nitrogen, or percent oxygen.

With further reference to FIG. 5, a standard deviation of at least one of the two or more molecular properties is calculated. (See 508). For example, the standard deviation of $BP_{mean}$ can be calculated based on equation 7. Standard deviation can be calculated using any suitable method as known in the art. For example, the standard deviation of $BP_{mean}$ can be defined as:

$$\sigma_{BP}(f) = 0.01 \Sigma\Sigma\Sigma w_0(f,T,MW,Z(X))(BP(T,MW,Z(X)) - (X-a(f))/b(f))^2 \quad (10)$$

Where the molecular formula distribution is defined as a fraction molecular formula distribution for each of a plurality of fractions, the standard deviation of at least one of the two or more molecular properties can be expressed as a fraction standard deviation for each of a plurality of fractions.

With further reference to FIG. 1, the initial molecular formula distribution can be extrapolated beyond the predetermined threshold along the correlation using at least one processor. (See 106). This process results in the generation of an extrapolated molecular formula distribution.

The extrapolation of the initial molecular function can be based on the correlation (e.g., Equation 7) and the standard deviation (e.g., Equation 10). For example, and for the purpose of understanding, in one embodiment, the initial molecular formula distribution and the correlation can be plotted on a graph. The initial molecular formula can then be extended along a line defined by the correlation above the predetermined threshold. Such extension can be constrained by an upper bound and a lower bound determined based on the standard deviation. For example, the bounds can be determined as:

$$BP = BP_{mean}(X) \pm 3\sigma_{BP} \quad (11)$$

An example of a correlation graph is shown in FIG. 6. The initial molecular formula distribution for each of seven LC fractions is shown in FIGS. 6(a)-(g). FIG. 6a is the graph for the DAO ARC1 fraction. FIG. 6b is the graph for the DAO ARC2 fraction. FIG. 6b is the DAO ARC3 fraction. FIG. 6d is the DAO ARC4 fraction. FIG. 6e is the DAO sulfides fraction. FIG. 6f is the DAO polars fraction. FIG. 6g is the asphaltenes fraction. The middle line 602 in each graph is the line defined by the correlation, the upper line 604 is the upper bound, and the lower line 606 is the lower bound. The molecular formula distributions for each of the LC fractions cuts off at around 1200° F. Thus, the initial molecular formulas for each of the LC fractions can be extended beyond the boiling point threshold in order to construct the extrapolated molecular formula distribution.

Figure 7:
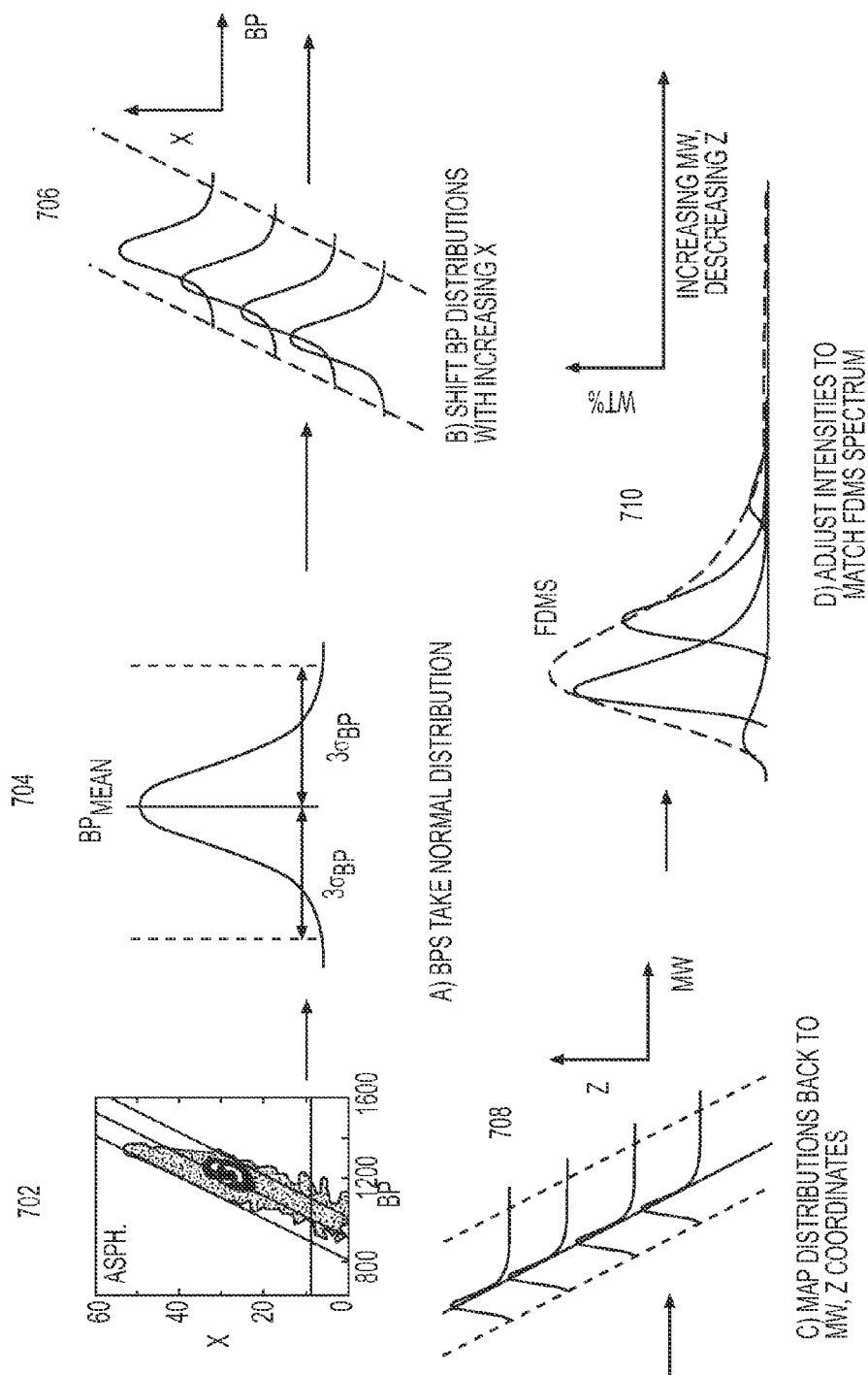
FIG. 7 is a flow a schematic representation of a method of extrapolating an initial molecular formula distribution beyond a predetermined threshold in accordance with the disclosed subject matter.

An exemplary method for extrapolating the initial molecular formula distribution is shown in FIG. 7 for illustration and not limitation. The method starts with a correlation 702 similar to the correlations shown in FIG. 6. The correlation can be, for example, based on Equation 7.

The initial molecular formula can then be extrapolated by calculating a normal distribution for a first molecular property. For example, a normalized boiling point distribution 704 can then be determined. The normalized boiling point distribution can be defined as:

$$w_{BP}(f, X, BP) = \frac{1}{\sqrt{2\pi}\sigma_{BP}(f)} \exp\left(-\frac{(BP - BP_{mean})^2}{2\sigma_{BP}^2(f)}\right) \quad (12)$$

As described herein, boiling point distribution can be truncated three standard deviations away from the mean boiling point, such that:

$$W_{BP}(f, X, BP) = 0 \text{ for } BP < BP_{mean} \pm 3\sigma_{BP}(f) \quad (13)$$

The normalized boiling point distribution can be calculated for every value of the first molecular property (e.g., the convenient molecular property X=0, 1, 2 . . . ) up to a threshold value. (See 706). Thus, distributions with an increasing $BP_{mean}$ can be generated. The threshold value can be based on the peak value of the normalized boiling point distribution (or the molecular weight distribution, which is related to the normalized boiling point distribution).

The plurality of normalized boiling point distributions can then be mapped from a first space to a second space. (See 708). For example, as shown in FIG. 7, a boiling point distribution 706 can be mapped to a distribution of nominal molecular weights 708 (e.g., from the (X, BP) space to the (MW, Z) space). The mapping of the boiling point distribution to a molecular weight distribution in such an embodiment satisfies:

$$w_{MW}(f,MW,Z,(X,T),T) = W_{BP}(f,X,BP(MW,Z,T)) \quad (14)$$

As previously noted, the dependence of boiling point BP on molecular weight MW can be a non-linear function. As such, the molecular weight distribution can have a non-normal distribution. (See 708).

With reference to FIG. 1, the extrapolated molecular formula distribution is renormalized based on renormalization data obtained from the sample to generate a renormalized molecular formula distribution. (See 108). Renormalization data can include, for example, molecular weight distribution data (e.g., field-desorption mass spectrometry data), boiling point distribution data (e.g., GC-Simdis data), and molecular type distribution data (e.g., FTICR-MS data). The type of data used as renormalization data will usually depend on the correlated molecular properties. Examples of paired combinations of molecular properties and renormalization data are shown in Table 3.

TABLE 3

| Molecular Property(s) | Renormalization Data |
|---|---|
| Z, BP of sample | FDMS of sample |
| Z, BP, molecular type | FDMS of sample |
| Z, MW, molecular type | GC-Simdis of sample |
| Z, BP of each LC fraction | FDMS of each LC fraction |
| Z, MW of each LC fraction | FDMS of each LC fraction |
| Z or MW of each LC fraction | GC-Simdis of each LC fraction |
| Z or BP of each LC fraction | FDMS of each LC fraction |

Figure 8:
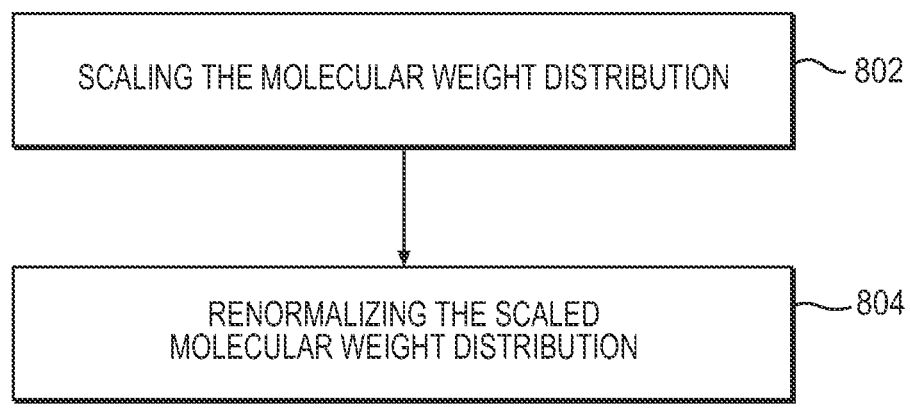
FIG. 8 is a flow chart of a representative embodiment of a method of renormalizing the extrapolated molecular formula distribution in accordance with the disclosed subject matter.

With reference to FIG. 8, a method for renormalizing the extrapolated molecular formula distribution can include scaling the molecular weight distribution. (See 802). The molecular weight distribution $w_{MW}(f,MW,Z,T)$ can be rescaled such that the abundance at the peak molecular weight $MW_{max}(f,Z,T)$ matches that of the FDMS spectrum. Thus, the molecular weight distribution can be scaled as:

$$w_{MWscaled}(f, MW, Z, T) = \frac{w_{FDMS}(F, MW_{max})}{w_{MW}(f, MW, Z, T)} w_{MW}(f, MW, Z, T) \quad (15)$$

The scaled molecular formula distribution is then renormalized. (See 804). The total abundance by molecular type T within each fraction of the renormalized molecular formula distribution can be matched to the total abundance by molecular type T within each fraction of the initial molecular formula distribution. The total abundance used for matching can be the total abundance of a measurement of the petroleum sample (e.g., a FTICR-MS measurement). For example, the renormalized molecular formula distribution can be defined as:

$$w_{Renormalized}(f, MW, Z, T) = \frac{\sum_{MW}\sum_{Z} w_0(f, MMW, Z, T)}{\sum_{MW}\sum_{Z} w_{MWscaled}(f, MW, Z, T)} w_{MWscaled}(f, MW, Z, T) \quad (16)$$

Figure 9:
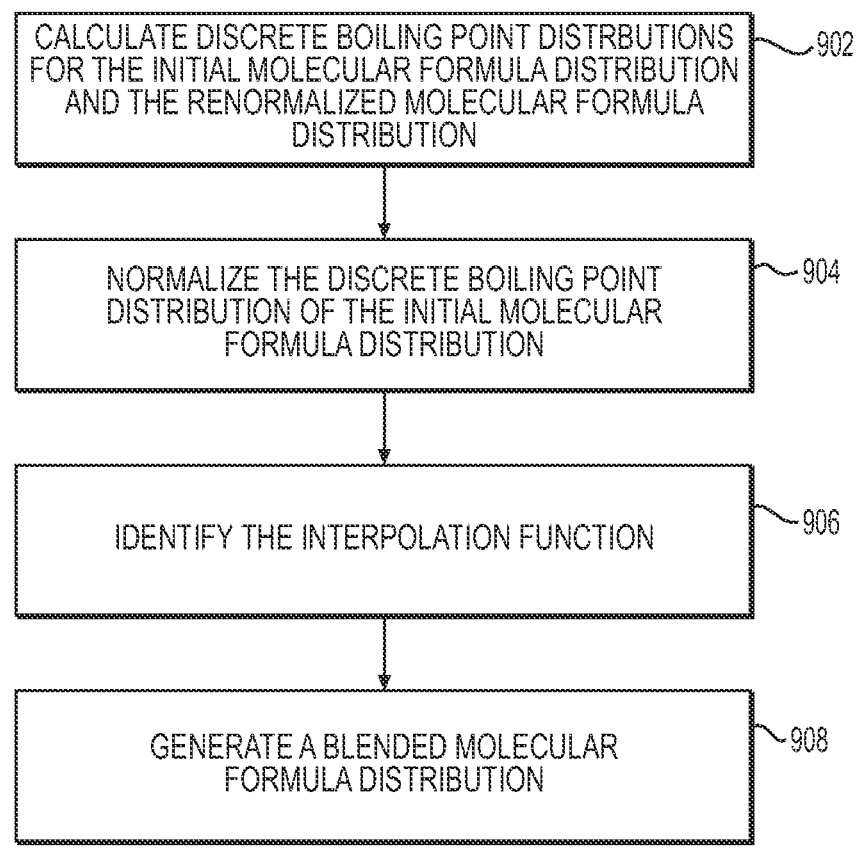
FIG. 9 is a flow chart of a representative embodiment of a method of blending the initial molecular formula distribution with the renormalized molecular formula distribution in accordance with one embodiment of the disclosed subject matter.

The extrapolation described herein provides improved results for molecular boiling points over 1250° F. Furthermore, to maintain a similar level of detail contained in the initial molecular formula distribution at boiling points below 1250° F., the renormalized molecular formula distribution can be blended with the initial molecular formula distribution. For example, and not limitation, a method for blending the renormalized molecular formula distribution with the initial molecular formula distribution is shown in FIG. 9. First, discrete boiling point distributions are determined for the initial molecular formula distribution and the renormalized boiling point distribution. (See 902). For example, and not limitation, the discrete boiling point distributions can be calculated using Equations 17 and 18.

$$W_0(f, B) = \sum_{MW}\sum_{Z}\sum_{T} w_0(f, MW, Z, T)\delta|BP(f, MW, Z, T) - B| < 20) \quad (17)$$

$$W_{Renormalized}(f, B) = \sum_{MW}\sum_{Z}\sum_{T} w_{Renormalized}(f, MW, Z, T)\delta|BP(f, MW, Z, T) - B| < 20) \quad (18)$$

where boiling points, BP, are computed molecular formula using the EDL-III property correlation, δ is the Dirac delta function, and the discrete boiling points, B, are in 20° F. increments:

$$B = 700 + 20k \text{ for } k = 0, 1, 2, \quad (19)$$

Figure 10C:
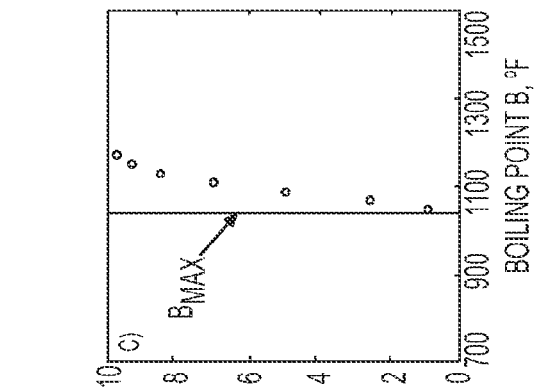
FIG. 10c is a graph showing the blended molecular formula distribution.
Figure 10B:
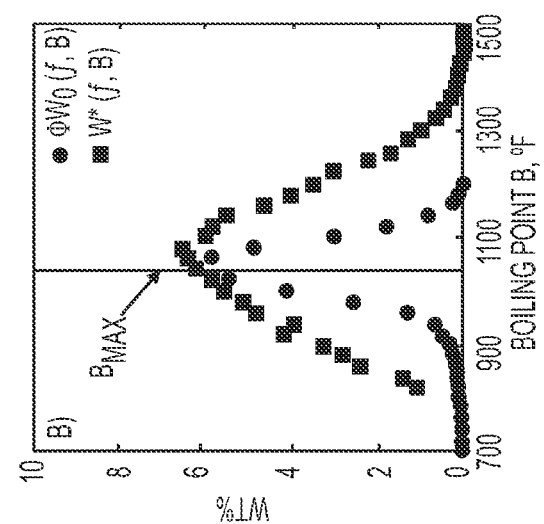
Figure 10A:
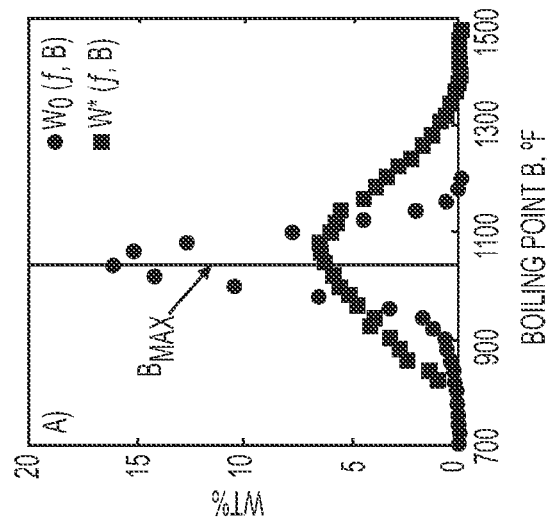

An example of the discrete boiling points distributions is shown in FIG. 10. The discrete boiling point distribution for the initial molecular formula distribution (the first discrete distribution) is plotted in FIG. 10a using circles, while the discrete boiling point distribution for the renormalized molecular formula distribution (the second discrete distribution) is plotted using squares.

The discrete boiling point distribution of the initial molecular formula distribution (the first discrete distribution) is then normalized. (See 904). As embodied herein, the peak abundance of the normalized discrete boiling point distribution of the initial molecular formula (the normalized first discrete distribution) is matched to the peak abundance of the discrete boiling point distribution of the renormalized molecular formula distribution (the second discrete distribution). The normalization faction is defined as:

$$\Phi = W_{Renormalized}(f, B_{max})/W_0(f, B_{max}) \quad (20)$$

where $B_{max}$ is the discrete boiling point that maximizes the distribution $W_0(f,B)$. The normalized boiling point distribution, $\Phi W_0(f,B)$ is shown in FIG. 10b (plotted using circles).

With reference to FIG. 9, an interpolation function for generating a blended molecular formula distribution can then be identified based on the normalized first discrete distribution and the second discrete distribution. (See 906). A single interpolation function can be defined for the entire range of boiling points. Alternatively, two or more interpolation functions can be defined over discrete boiling point ranges. For example, in one embodiment, the interpolation function $\Phi(f,B)=0$ for all boiling points below $B_{max}$. For all boiling points above $B_{max}$, the interpolation function is defined as:

$$\phi(f,B) = 1 \Phi W_0(f,B)/W_{Renormalized}(f,B) \quad (21)$$

With further reference to FIG. 9, a blended molecular formula distribution can be generated based on the interpolation function. (See 908). An exemplary blended molecular formula distribution is shown in FIG. 10c.

Figure 11:
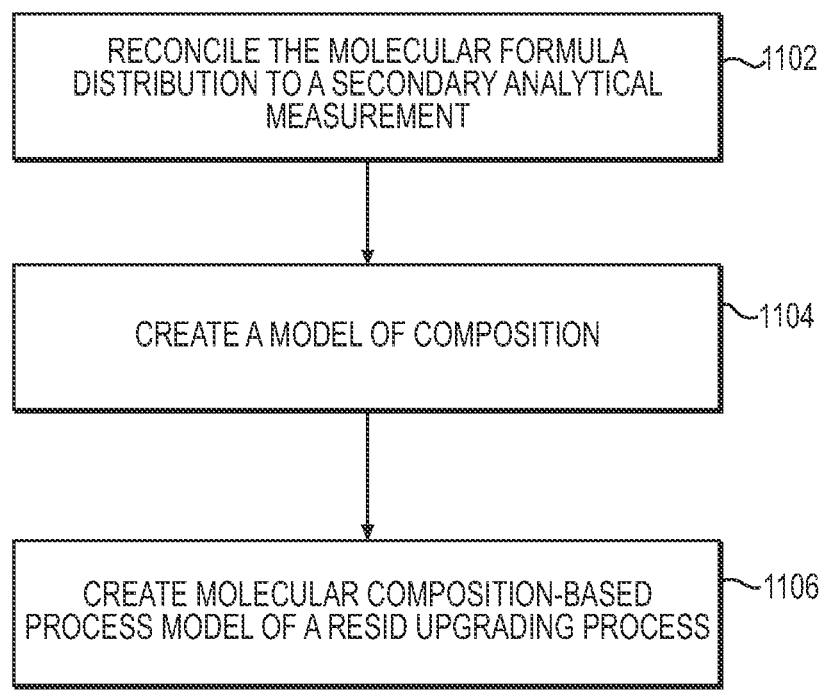
FIG. 11 is a flow chart of a representative embodiment of a method of creating a molecular composition-based process model of a resid upgrading process in accordance with the disclosed subject matter.

In accordance with the disclosed methods, further adjustments can be made to the molecular formula distribution as desired. FIG. 11 illustrates additional modifications and uses for the renormalized and/or blended molecular formula distribution in accordance with the disclosed subject matter. For example, a reconciliation process can be used to reconcile the molecular formula distribution with a secondary analytical measurement. (See 1102). The secondary analytical measurement can include, for example, super critical fluid chromatography, sulfur simulated distillation, simulated distillation, N and S elemental analysis, H-NMR and GC-Flame Ionization Detection. Further information about this process is described in U.S. Patent Publication No. 2009/0105966, filed on Oct. 10, 2008, which is incorporated herein by reference in its entirety. The molecular formula distribution can be reconciled with the secondary analytical measurement according to the co-pending U.S. Provisional Patent Application No. 61/653,069, filed on May 30, 2012, entitled "Method for Reconciling a Model of Composition," the disclosure of which is incorporated herein by reference in its entirety.

Additionally or alternatively, the molecular formula distribution resulting from the various methods described herein can be used to create a model of composition. (See 1104). For example, a model of composition can be created based on the reconciled molecular formula distribution. For each molecular formula in a molecular formula distribution, a molecular structure or structure-oriented lump, e.g., group of data, can be assigned to the formula. The structures or structure-oriented lumps can be used as a model of composition.

In this manner, the model of composition can then be used to create a molecular-composition based process model of a resid upgrading process. (See 1106). The resid upgrading process can be, for example, a thermal cracking (coking) process, a propane-deasphalting process, or a hydroprocessing process.

Although the method described herein refers to graphical mapping and plotting techniques, for purpose of illustration and demonstration, alternative mathematics can be used without requiring graphical display. Furthermore, the method or steps thereof can be performed using a processor or other systems.

Figure 12:
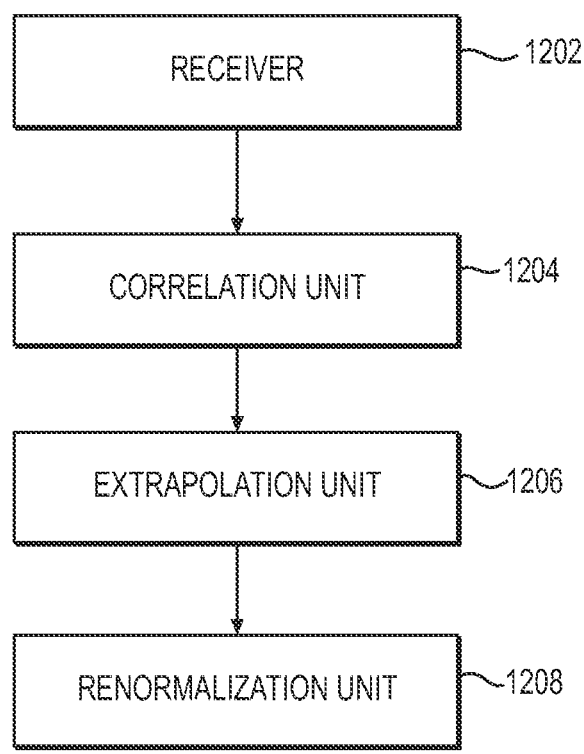
FIG. 12 is a schematic representation of a system for extrapolating a molecular formula distribution beyond a predetermined threshold in accordance with the disclosed subject matter.

FIG. 12 illustrates a representative embodiment of a system for extrapolating a molecular formula distribution beyond a predetermined threshold in accordance with the disclosed subject matter. For purpose of illustration, and not limitation, the system embodied herein includes a receiver 1202, a correlation unit 1204, an extrapolation unit 1206, and a renormalization unit 1208. Additionally, a user interface 1210 can be included in the system.

Each of the components of the system can implemented as hardware or a combination of hardware and software. In the exemplary embodiment, at least some of the components constitute a physical device (i.e., hardware) that responds to instructions embodied in software. For example, the correlation unit 1204 can be one or more processors that are programmed with instructions that, when executed, cause the one or more processors to identify a correlation between two or more molecular properties of the initial molecular formula distribution. The instructions can be written in code. The term "code," as used herein, embraces both source code and object code. The instructions can be embodied in a computer readable medium. The term "computer-readable medium" includes any mechanism for storing or transmitting information in a form readable by a computer. For example, a computer-readable medium includes, but is not limited to, read only memory ("ROM"), random access memory ("RAM"), magnetic disk storage media, optical storage media, flash memory devices, etc.

The receiver 1202 is configured to obtain an initial molecular formula within a predetermined threshold from a sample of the petroleum stream. The receiver 1202 can receive the initial molecular formula from a third party. The molecular formula can be received, for example, over a communications network such as the Internet, or from a memory device such as a CD-ROM or a flash memory device. The receiver can also be logically connected to a user interface, and the receiver can obtain the molecular formula distribution from the information entered by the user. Alternatively, the receiver can receive information from a third party and generate an initial molecular formula based on that information. For example, the receiver can receive FTICR-MS data. The receiver can also have a seeding subunit for seeding the initial molecular formula with additional molecules to generate a seeded molecular formula, as discussed herein. In general, the receiver can be any suitable component as known in the art.

While no direct connection is shown between receiver 1202 and the extrapolation unit 1208, it will be understood by those skilled in the art that each of the components shown in FIG. 12 can be communicably connected to each other. Moreover, any of the components of the system can also be directly connected to any other component without negatively affecting the operability of the system.

The correlation unit 1204 is configured to identify a correlation between two or more molecular properties of the initial molecular formula distribution. The correlation unit can be connected to a user interface which allows the user to determine the molecular properties and/or the equation to be used in identifying the correlation. Alternatively, the correlation unit 1204 can be programmed to use a certain group of molecular properties and/or a particular equation to identify the correlation (i.e., the two or more molecular properties and/or the equation can be predetermined). The correlation unit can include a coefficient calculation unit for calculating the coefficients of the equation. The correlation unit 1204 can also include a standard deviation unit for calculating the standard deviation of at least one of the two or more molecular properties.

The extrapolation unit 1206 is configured to extrapolate the initial molecular formula distribution beyond the predetermined threshold along the correlation to construct an extrapolated molecular formula distribution. The extrapolation unit 1206 can include components for extending the initial molecular formula distribution along a line defined by the correlation, wherein the extended molecular formula distribution is bounded by an upper bound and a lower bound defined by the standard deviation of at least one of the two or more molecular properties. The extrapolation unit 1206 can include a normalizing unit for calculating a normal distribution of a first molecular property and a mapping unit configured to map the normal distribution of the first molecular property from a first space to a second space.

The renormalization unit 1208 is configured to renormalize the extrapolated molecular formula distribution based on renormalization data obtained from the sample to generate a renormalized molecular formula distribution. The renormalization unit 1208 can include a scaling unit configured to scale the molecular formula distribution and a matching unit to match the total abundance by molecular type of the extrapolated molecular formula distribution with a total abundance of a measurement of the sample. The renormalization can be obtained by the receiver 1202, or by a separate receiver.

The user interface 1210 allows a user to receive information from and/or provide information to the system. For example, the user interface 1210 can include a display or the like in order to allow the system to provide information related to, for example, a renormalized molecular formula distribution, a model of composition, or a molecular-composition based process model of a resid upgrading process. Alternatively or additionally, the user interface 1210 can include a controller to implement controls based on user input.

In summary, the system includes the various components and units suitable to perform the method as described in detail herein. The system can also include other components. For example, the system can include a memory device for storing data. The stored data can include FTICR-MS data, FDMS data, the initial molecular formula distribution, the extrapolated molecular formula distribution, and any other data received or generated by the system. The memory device can be any device that stores data. Examples of memory devices that can be used include internal hard drives, external hard drives, and removable storage devices such as compact discs, USB drives, and the like. In general, the memory device can be any suitable storage device as known in the art.

The system can also include other hardware and/or software components for implemented the disclosed subject matter. For example, the system can additionally include a blending unit, a model generation unit, a reconciling unit, a process designing unit, and any other module for implementing the disclosed methods.

Those having skill in the art will recognize that, while many of the components of the system have been identified as a subcomponent of a larger component, each of the subcomponents of the system can be implemented by separate processors. For example, the seeding subunit of the receiver can be implemented either on the same processor as the receiver, or on a different processor. Moreover, each of the components described herein can likewise be implemented on a single processor. Thus, the system as a whole, as well as each of, for example, the receiver, the correlation unit, the extrapolation unit, and the renormalization unit, can be implemented using one or more processors.

While the present application is described herein in terms of certain preferred embodiments, those skilled in the art will recognize that various modifications and improvements can be made to the application without departing from the scope thereof. Thus, it is intended that the present application include modifications and improvements that are within the scope of the appended claims and their improvements. Moreover, although individual features of one embodiment of the application may be discussed herein or shown in the drawings of one embodiment and not in other embodiments, it should be apparent that individual features of one embodiment can be combined with one or more features of another embodiment or features from a plurality of embodiments.

In addition to the specific embodiments claimed below, the application is also directed to other embodiments having any other possible combination of the dependent features claimed below and those claimed above. As such, the particular features presented in the dependent claims and disclosed above can be combined with each other in other manners within the scope of the application such that the application should be recognized as also specifically directed to other embodiments having any other possible combinations. Thus, the foregoing description of specific embodiments of the application has been presented for purposes of illustration and description. It is not intended to be exhaustive or to limit the application to those embodiments disclosed.

The invention claimed is:

1. A method to generate molecular formula distributions beyond a predetermined threshold for a petroleum stream, the method comprising:
   obtaining a sample from the petroleum stream;
   separating the petroleum stream into a plurality of fractions;
   obtaining an initial molecular formula distribution within the predetermined threshold for the sample of the petroleum stream; wherein the initial molecular formula distribution comprises a fraction molecular formula distribution for each of the plurality of fractions;
   identifying a correlation between two or more molecular properties of the initial molecular formula distribution;
   extrapolating, using at least one processor, the initial molecular formula distribution beyond the predetermined threshold along the correlation to construct an extrapolated molecular distribution, wherein the predetermined threshold is a predetermined hydrogen deficiency threshold; and
   renormalizing the extrapolated molecular formula distribution based on renormalization data obtained from the sample to generate a renormalized molecular formula distribution.

2. The method of claim 1, wherein obtaining the initial molecular formula distribution comprises using an analytical technique.

3. The method of claim 2, wherein the analytical technique is one of high-detail hydrocarbon analysis, microhydrocarbon analysis, and ultrahigh resolution Fourier transform ion Cyclotron Resonance mass spectrometry.

4. The method of claim 2, wherein the analytical technique is a multivariate analytical technique.

5. The method of claim 1, wherein obtaining an initial molecular formula distribution comprises using a modeling technique.

6. The method of claim 5, wherein the modeling technique is one of composition based process modeling, composition synthesis, and theory-based.

7. The method of claim 1, wherein each of the plurality of fractions is a liquid chromatographic fraction.

8. The method of claim 1, wherein the plurality of fractions comprise at least one of deasphalted oil saturates, deasphalted oil aromatic ring class 1, deasphalted oil aromatic ring class 2, deasphalted oil aromatic ring class 3, deasphalted oil aromatic ring class 4, deasphalted oil sulfides, deasphalted oil polars, asphaltenes, deasphalted oil aromatics, and deasphalted oil.

9. The method of claim 1, further comprising
   seeding the initial molecular formula distribution with at least one metal containing molecule.

10. The method of claim 9, wherein said at least one metal containing molecule comprises at least one of a nickel-containing porphyrin and a vanadium-containing porphyrin.

11. The method of claim 1, wherein the two or more molecular properties comprise at least one of hydrogen deficiency, boiling point, molecular weight, molecular fraction, and molecular type.

12. The method of claim 1, wherein the renormalization data obtained for the sample is one of field desorption mass spectrometry FDMS, BP distribution, GC-Simdis, and molecular type distribution.

13. The method of claim 1, further comprising
   reconciling the renormalized molecular formula distribution with a secondary analytical measurement.

14. The method of claim 13, wherein the secondary analytical measurement is a measurement using one of super critical fluid chromatography, sulfur simulated distillation, simulated distillation, N and S elemental analysis, Proton Nuclear Magnetic Resonance Spectroscopy H-NMR and GC-Flame Ionization Detection.

15. The method of claim 13, further comprising creating a model of composition based on the reconciled molecular formula distribution.

16. The method of claim 1, further comprising creating a molecular-composition based process model of a resid upgrading process.

17. The method of claim 16, wherein the resid upgrading process comprises one of thermal cracking (coking), propane-deasphalting, and hydroprocessing.

18. A method to generate molecular formula distributions beyond a predetermined threshold for a petroleum stream the method comprising:
   obtaining a sample from the petroleum stream;
   separating the petroleum stream into a plurality of fractions;
   obtaining an initial molecular formula distribution within the predetermined threshold for the sample of the petroleum stream; wherein the initial molecular formula distribution comprises a fraction molecular formula distribution for each of the plurality of fractions;
   identifying a correlation between two or more molecular properties of the initial molecular formula distribution, wherein identifying the correlation between two or more molecular properties comprises calculating a coefficient of an equation defining a first molecular property as a function of a second molecular property;
   extrapolating, using at least one processor, the initial molecular formula distribution beyond the predetermined threshold along the correlation to construct an extrapolated molecular distribution; and
   renormalizing the extrapolated molecular formula distribution based on renormalization data obtained from the sample to generate a renormalized molecular formula distribution.

19. The method of claim 18, wherein the coefficient is calculated using a least squares analysis.

20. The method of claim 18, further comprising calculating a standard deviation of at least one of the two or more molecular properties.

21. The method of claim 20, wherein calculating a standard deviation of at least one of the two or more molecular properties comprises calculating a fraction standard deviation for each of a plurality of fractions.

22. The method of claim 18, wherein the equation is X=a+b*BP, where X=(mod(Z,2)−Z)/2.

23. The method of claim 18, wherein the equation is selected to conserve a desired property of the petroleum stream.

24. The method of claim 23, wherein the desired property is one of hydrogen content, percent aromatic carbon, heteroatom content, and solubility parameter.

25. The method of claim 18, wherein the equation is a non-linear equation.

26. The method of claim 18, wherein the predetermined threshold is one of a predetermined boiling point threshold, a predetermined molecular weight threshold, and a predetermined hydrogen deficiency threshold.

27. A method to generate molecular formula distributions beyond a predetermined threshold for a petroleum stream, the method comprising:
obtaining a sample from the petroleum stream;
separating the petroleum stream into a plurality of fractions;
obtaining an initial molecular formula distribution within the predetermined threshold for the sample of the petroleum stream; wherein the initial molecular formula distribution comprises a fraction molecular formula distribution for each of the plurality of fractions;
identifying a correlation between two or more molecular properties of the initial molecular formula distribution;
extrapolating, using at least one processor, the initial molecular formula distribution beyond the predetermined threshold along the correlation to construct an extrapolated molecular distribution, wherein extrapolating the initial molecular formula distribution comprises calculating a normal distribution for a first molecular property; and
renormalizing the extrapolated molecular formula distribution based on renormalization data obtained from the sample to generate a renormalized molecular formula distribution.

28. The method of claim 27, wherein extrapolating the initial molecular formula distribution further comprises mapping the normal distribution of the first molecular property from a first space to a second space.

29. The method of claim 27, wherein the predetermined threshold is one of a predetermined boiling point threshold, a predetermined molecular weight threshold, and a predetermined hydrogen deficiency threshold.

30. A method to generate molecular formula distributions beyond a predetermined threshold for a petroleum stream, the method comprising:
obtaining a sample from the petroleum stream;
separating the petroleum stream into a plurality of fractions;
obtaining an initial molecular formula distribution within the predetermined threshold for the sample of the petroleum stream; wherein the initial molecular formula distribution comprises a fraction molecular formula distribution for each of the plurality of fractions;
identifying a correlation between two or more molecular properties of the initial molecular formula distribution;
extrapolating, using at least one processor, the initial molecular formula distribution beyond the predetermined threshold along the correlation to construct an extrapolated molecular distribution, wherein extrapolating the initial molecular formula distribution comprises extending the initial molecular formula distribution along a line defined by the correlation; and
renormalizing the extrapolated molecular formula distribution based on renormalization data obtained from the sample to generate a renormalized molecular formula distribution.

31. The method of claim 30, wherein the extrapolated molecular distribution is bounded by an upper bound and a lower bound calculated based on the line and a standard deviation of at least one of the two or more molecular properties.

32. The method of claim 30, wherein the predetermined threshold is one of a predetermined boiling point threshold, a predetermined molecular weight threshold, and a predetermined hydrogen deficiency threshold.

33. A method to generate molecular formula distributions beyond a predetermined threshold for a petroleum stream, the method comprising:
obtaining a sample from the petroleum stream;
separating the petroleum stream into a plurality of fractions;
obtaining an initial molecular formula distribution within the predetermined threshold for the sample of the petroleum stream; wherein the initial molecular formula distribution comprises a fraction molecular formula distribution for each of the plurality of fractions;
identifying a correlation between two or more molecular properties of the initial molecular formula distribution;
extrapolating, using at least one processor, the initial molecular formula distribution beyond the predetermined threshold along the correlation to construct an extrapolated molecular distribution; and
renormalizing the extrapolated molecular formula distribution based on renormalization data obtained from the sample to generate a renormalized molecular formula distribution, wherein renormalizing the extrapolated molecular formula distribution based on the renormalization data comprises:
scaling the extrapolated molecular formula distribution; and
matching a total abundance by molecular type of the extrapolated molecular formula distribution with a total abundance of a measurement of the sample.

34. The method of claim 33, wherein the measurement is Fourier Transform Ion Cyclotron Resonance mass spectrometry FTICR-MS.

35. The method of claim 33, wherein the predetermined threshold is one of a predetermined boiling point threshold, a predetermined molecular weight threshold, and a predetermined hydrogen deficiency threshold.

36. A method to generate molecular formula distributions beyond a predetermined threshold for a petroleum stream, the method comprising:
obtaining a sample from the petroleum stream;
separating the petroleum stream into a plurality of fractions;
obtaining an initial molecular formula distribution within the predetermined threshold for the sample of the petroleum stream; wherein the initial molecular formula distribution comprises a fraction molecular formula distribution for each of the plurality of fractions;
identifying a correlation between two or more molecular properties of the initial molecular formula distribution;
extrapolating, using at least one processor, the initial molecular formula distribution beyond the predetermined threshold along the correlation to construct an extrapolated molecular distribution;

renormalizing the extrapolated molecular formula distribution based on renormalization data obtained from the sample to generate a renormalized molecular formula distribution; and blending the renormalized molecular formula distribution with the initial molecular formula distribution.

37. The method of claim 36, wherein blending the renormalized molecular formula distribution with the initial molecular formula distribution comprises:

determining a first discrete distribution for the initial molecular formula distribution and a second discrete distribution for the renormalized molecular formula distribution;

normalizing the first discrete distribution by matching a peak abundance of the normalized first discrete distribution with a peak abundance of the second discrete distribution;

identifying an interpolation function based on the normalized first discrete distribution and the second discrete distribution; and generating a blended molecular formula distribution based on the interpolation function.

* * * * *